United States Patent [19]

O'Neil

[11] Patent Number: 4,739,928

[45] Date of Patent: Apr. 26, 1988

[54] AIR FRESHENER DISPENSER

[75] Inventor: William J. O'Neil, Cincinnati, Ohio

[73] Assignee: The Drackett Company, Cincinnati, Ohio

[21] Appl. No.: 27,094

[22] Filed: Mar. 13, 1987

Related U.S. Application Data

[63] Continuation of Ser. No. 787,275, Oct. 15, 1985, abandoned.

[51] Int. Cl.$^4$ .............................................. A61L 9/04
[52] U.S. Cl. ........................................ 239/45; 239/47; 239/51.5
[58] Field of Search .................................... 239/42–47, 239/49–51, 51.5, 53–60, 326

[56] References Cited

U.S. PATENT DOCUMENTS

| | | |
|---|---|---|
| 472,133 | 5/1892 | Merrill . |
| 525,646 | 9/1894 | Cox . |
| 1,332,659 | 3/1920 | Bates . |
| 1,377,909 | 5/1921 | Moulin ................................ 239/45 |
| 1,860,658 | 7/1932 | Lichtig . |
| 1,974,414 | 9/1934 | Dupuy ............................ 239/45 X |
| 2,383,960 | 9/1945 | Dupuy ............................ 239/59 X |
| 2,412,326 | 12/1946 | Dupuy . |
| 2,456,244 | 12/1948 | Bash ................................... 239/49 |
| 2,471,949 | 5/1949 | Gilowitz . |
| 2,554,302 | 5/1951 | Keskitalo . |
| 2,631,890 | 3/1953 | Fink . |
| 3,527,405 | 9/1970 | Harding . |
| 3,550,853 | 12/1970 | Gray . |
| 3,727,840 | 4/1973 | Nigro . |
| 4,154,398 | 5/1979 | Gualandi ............................... 239/59 |
| 4,165,835 | 8/1979 | Dearling . |
| 4,293,095 | 10/1981 | Hamilton et al. . |
| 4,323,193 | 4/1982 | Compton et al. . |
| 4,372,490 | 2/1983 | Le Caire, Jr. et al. ............... 239/59 |
| 4,477,414 | 10/1984 | Muramoto et al. . |
| 4,549,693 | 10/1985 | Barlics ................................... 239/58 |

OTHER PUBLICATIONS

Packaging, Rorian Sweet Cherry Liquid Toilet Fragrance (w/Translation Back Panel).
Packaging, Air Wick Constante Liquid Air Freshener (w/Translation Back Panel).
Packaging, Sharudan Fresh (liquid) Green Fragrance (w/Translation Front and Back Panels).

*Primary Examiner*—Andres Kashnikow
*Attorney, Agent, or Firm*—Charles J. Zeller

[57] ABSTRACT

An air freshener dispenser of the type containing in a reservoir a liquid fragrance composition comprising a necked container, a wick provided in the neck, an emanator pad holder retaining within a containment enclosure an absorbent or emanator pad in contact with the wick, and a cover member including at least one fragrance-diffusion aperture, the emanator pad holder including means defining at least one fragrance diffusion channel, the emanator pad being detachably rotatable within the cover member, whereby rotation of the cover member brings the diffusion aperture and the diffusion channel into registry.

21 Claims, 6 Drawing Sheets

AIR FRESHENER DISPENSER

This is a continuing application of application Ser. No. 787,275 filed Oct. 15, 1985, now abandoned.

FIELD OF INVENTION

The present invention relates to air freshener dispensers of the type containing in a reservoir a liquid fragrance composition that is carried to an emanator pad by wick means for subsequent diffusion from the pad to the atmosphere. More specifically, the present invention relates to an air freshener dispenser having a rotatable cover member overlaying an emanator pad holding means, said cover means being rotatable with respect to the pad holding means to open and close at least one fragrance-diffusion aperture in said cover means. Most specifically, the air freshener dispenser of the present invention includes means to retain the emanator pad holding means within the cover means, and means to detachably secure the emanator pad holding means to the reservoir.

BACKGROUND OF THE INVENTION

Fragrance diffusers including wick means to convey a volatile fragrance composition from a reservoir to the atmosphere directly or to an emanator pad for subsequent diffusion to the atmosphere are known. Thus, U.S. Pat. No. 1,332,659 to Bates illustrates an evaporimeter comprising a reservoir, a cylindrical, hollow shaft extending upwardly of the reservoir, and a perforated disk normal to the shaft, there being a wick within the shaft, the strands of the wick being spread across the disk, and a cover placeable over the disk. U.S. Pat. No. 4,477,414 to Muramoto et al. discloses a wickless evaporative container, the liquid in the reservoir being drawn up through a feed pipe rather than a wick. In the vaporizing device of Dupuy, U.S. Pat. No. 2,383,960, the reservoir has a wide-mouth orifice in which is inserted pad holding means, the pad thus held being in contact with a wick extending into the reservoir. A cover is superposed over the pad holding insert, apertures in the cover cooperating with apertures in the pad holding insert to provide adjustability of the air diffusion passages defined by the assembly.

U.S. Pat. No. 1,377,909 to Moulin discloses a container, a wick extending upwardly from the container through a holed-stopper, absorbent material in contact with the top of the wick, and an apertured cover affixed to an upstanding skirt of the container.

SUMMARY OF THE INVENTION

It is an object of the present invention to provide an adjustable air freshener dispenser of the wick type.

It is a further object of the present invention that the air freshener dispenser include emanator or absorbent pad holding means retained within the cover member for said unit.

It is another object of the present invention that the emanator pad holding means be attachable to the neck of the container.

Yet another object of the present invention is to provide adjustability of the diffusion rate of fragrance composition wicked to the emanator pad by rotational movement of the cover member relative to the location of the emanator pad holding means when same are connected to the neck of the container in operational position.

These and other objects and advantages of the present invention are described in greater detail below, with reference to the accompanying drawings. A summary of the invention follows.

The air freshener dispenser comprises a container having a neck, said container being a reservoir for a liquid fragrance-containing composition; a wick provided in the neck, the wick depending into the reservoir for contact with the fragrance-containing composition and extending upwardly above the neck; closure means for sealing the container during nonuse, said closure means being removable for use; emanator pad holding means detachably securable to the neck of the container, said holding means being superposable above the closure means in nonuse mode, and a cover member overlying the emanator pad holding means, and including means to retain the emanator pad holding means within said cover member, said cover member being rotatable with respect to said emanator pad holding means and the emanator pad holding means being substantially nonrotatable with respect to the emanator pad holding means-container assembly.

DESCRIPTION OF THE PREFERRED EMBODIMENT

Figure 1:
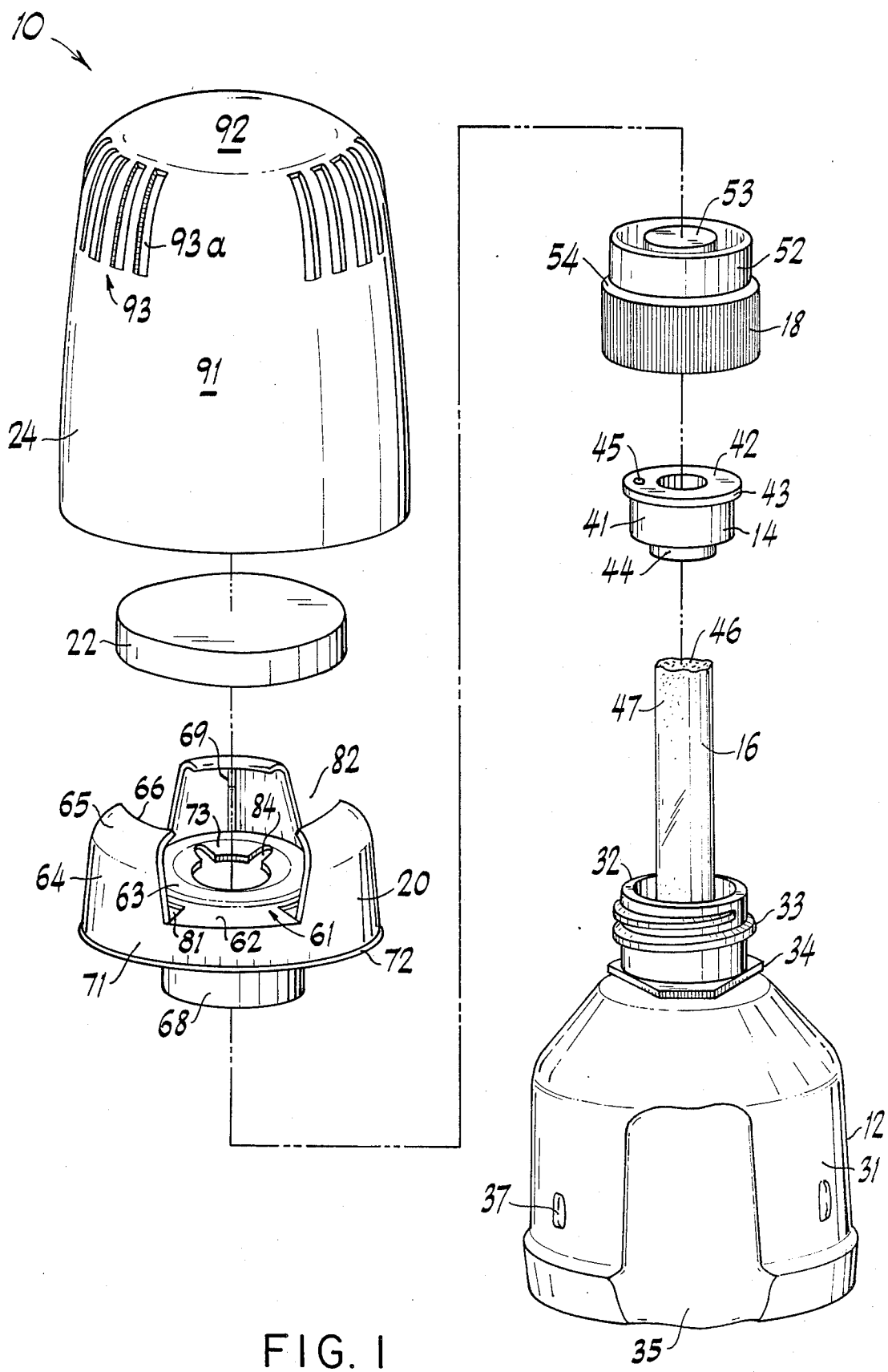
FIG. 1 is an exploded perspective view of the air freshener dispenser of the present invention.

Referring to FIG. 1, an exploded perspective view of the dispenser 10 of the present invention, the air freshener dispenser 10 comprises a container 12 for containing a volatile liquid fragrance composition, a neck insert member 14, a wick 16, a closure cap 18, an emanator pad holder 20, an emanator or absorbent pad 22, and a cover member 24.

The container 12 has a body 31 and a neck 32, the container 12 being a reservoir for the volatile air fragrance composition. The neck 32 includes threads 33, and below the threads a peripheral flange 34 shown herein as an octagonal flange. One or more land surfaces 37 are also included, the lands 37 frictionally engaging the cover member 24. The container can be fabricated by injection blow molding using a suitable plastic material, for example, polyethylene, polypropylene, and polyethylene terephthlate. A suitable capacity of the container is about 3–4 fluid ounces. The fragrance composition typically comprises a fragrance, an emulsifier, a volatile solvent, for example, isopropyl alcohol, optionally a colorant, and deionized water.

Figure 5:
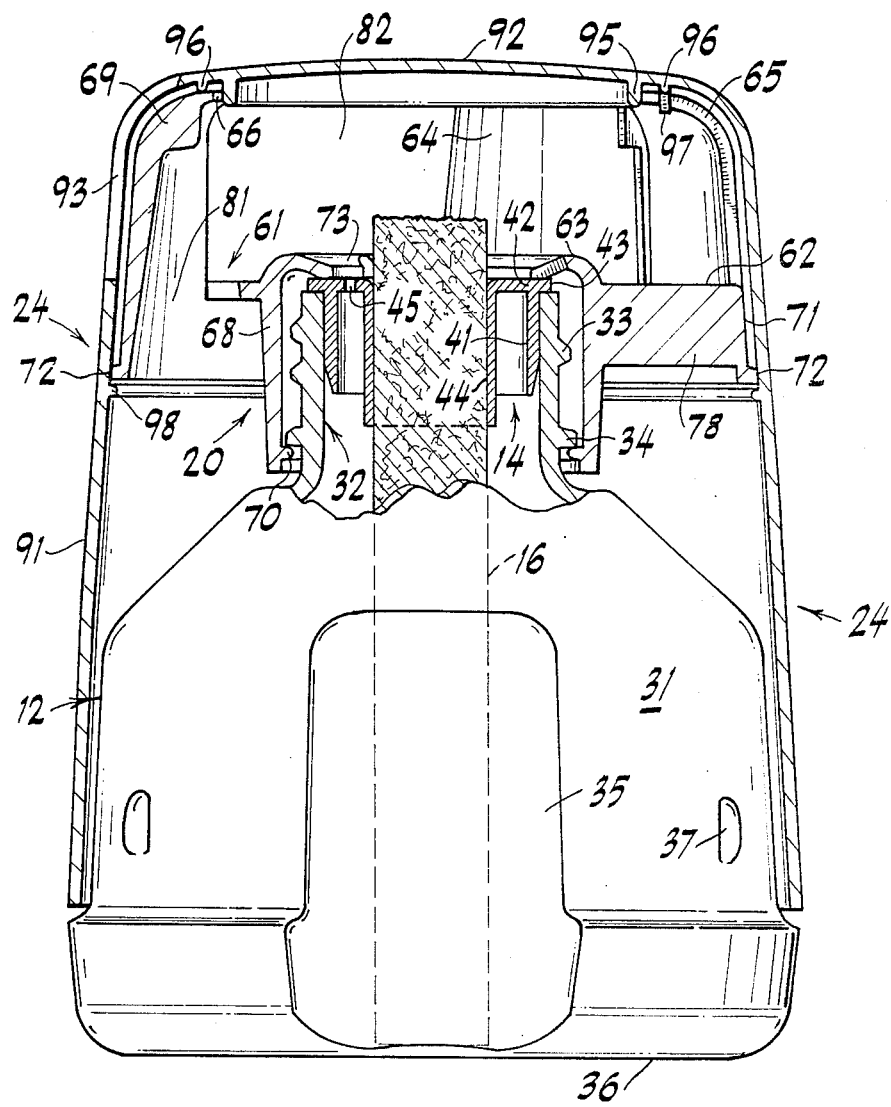
FIG. 5 is a vertical half-section cross-sectional view of the air freshener dispenser in its operational mode, the emanator pad omitted for clarity.

As illustrated in FIG. 1, and more specifically in the assembly FIG. 5, the insert member 14 is adapted for friction fit within the bore of the neck 32 of the container 12. The insert member 14 comprises an annular top portion 42 from which depends an outer annular skirt 41, said skirt 41 frictionally engaging the interior side wall of the neck 32. The top 42 of the insert member 14 includes an annular peripheral flange 43 that seats on the top edge of the neck 32. A vent hole 45 is also provided in the top 42. Also downwardly depending of the annular top portion 42 is a circular hollow shaft 44 that receives the wick 16. The wick 16 extends through the cylindrical shaft 44, the bottom end of which typically abuts the base 36 of the container. The wick 16 extends above the top 42 of the insert member 14 a predetermined distance. The wick preferably comprises an interior core 46 of an absorbent wicking material and an outer sheath 47 of a plastic material that prevents the strands of the absorbent material 46 from unravelling. Suitable materials include natural and synthetic fibers that are capable of being formed into a wick, for example, Scribrod ® manufactured by Baumgartner Papers S.A. The outer sheath 47 can be any wet-strength polymer capable of retaining the inner fibers, and may be permeable or nonpermeable. In the preferred embodiment, the absorbent fibers are polyester, and the outer sheath is a polyester film. The neck insert may be made, for example, of low-density polyethylene.

Figure 6:
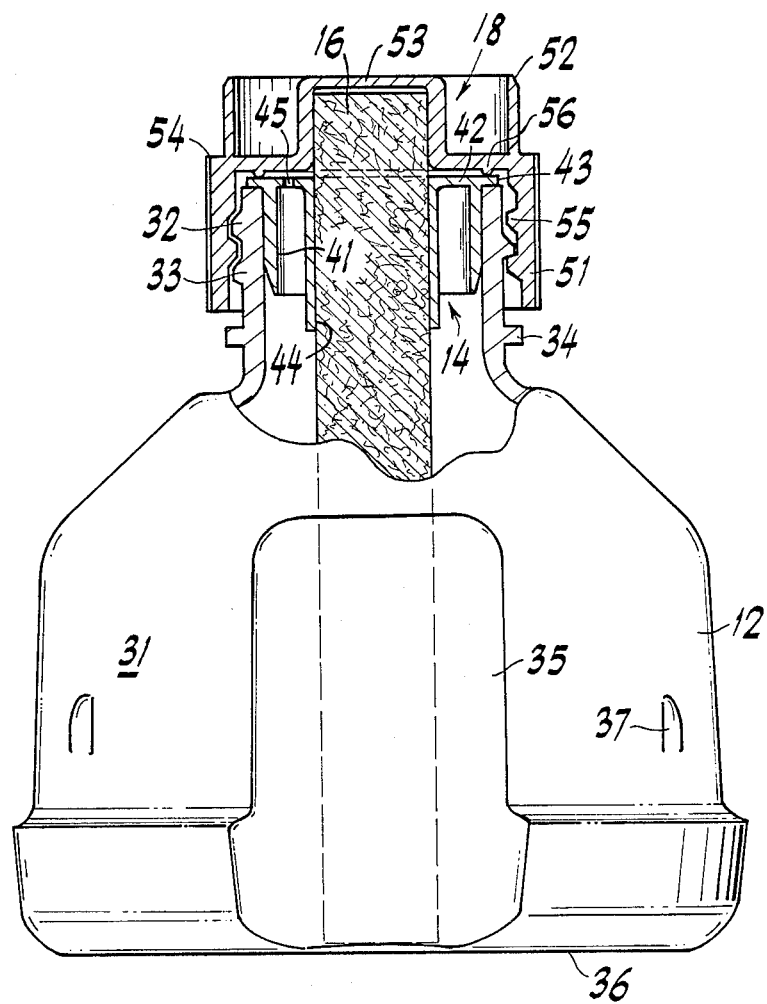
FIG. 6 is a partial vertical half-section cross-sectional view of the air freshener dispenser in its nonuse mode, the cover, emanator pad, and emanator pad holder having been omitted for clarity.

The closure cap 18 illustrated in nonuse assembly with the device in FIG. 6, as well as in FIG. 1, comprises a cylindrical body 51, the interior side wall of which is provided with threads 55 suitable for mating assembly with the threads 33 on the container neck 32. The closure cap 18 further includes an exterior upwardly extending skirt 52 forming with the cap body 51 an outer shoulder 54. Interior of the skirt 52 and extending upwardly of the cap body 51 is a dome member 53, the dome member being of suitable height to receive that portion of the scrib rod 16 extending above the top 42 of the neck insert 14.

As illustrated in FIG. 6, during nonuse the cap 18 is secured to the neck of the container 32 by means of the complementary threads 33 and 55 on the neck 32 and on the interior surface of the cap body 51, respectively. That portion of the wick 16 extending above the top 42 of the insert member 14 is received in the dome member 53. Suitable headspace is provided in dome member 53 so that the top of the wick does not come in contact with the top of the dome member 53. When sealed by the cap 18, the volatile fragrance composition cannot diffuse or otherwise escape from the container 12. A circular sealing boss 56 is dependingly interiorly provided on the top of the cap body 51 to provide a positive seal when the cap 18 is tightened about the neck 32 of the container 12.

The emanator pad holder 20 is next described with reference to FIGS. 1, 3, 4, and 5. The pad holder 20 comprises a base portion designated generally by numeral 61. The base portion 61 comprises a raised annular central portion 63 defining a large central aperture 80 and a plurality of spokelike portions 62 extending radially outwardly from the central portion 63 to the periphery of the emanator pad holder, the radial spokelike portions defining therebetween air circulation apertures 81. The pad holder 20 further comprises a peripheral skirt portion 71 that depends downwardly from the outermost periphery of the spokelike portions 62, the skirt portion 71 including proximate its bottom an exterior peripheral boss 72, the purpose of which is hereinafter described. Extending upwardly from the skirt portion 71 is a plurality of side wall segments 64, said side wall segments 64 being in radial alignment with and extending partially over the apertures 81, and forming therebetween a plurality of channels 82, said channels 82 being in radial alignment with the spokelike portions 62 of the base portion 61. Annular support portions 76 are provided between the central portion 63 and the interior edge 75 of the air circulation apertures 81.

The uppermost portion 65 of the side wall segments 64 is arcuately disposed towards the interior of the pad holder 20 and terminates in annular arcuate edges 66. The side walls 77 of the wall segments 64 including the arcuate portion 65 are tapered so that the bottom of the side wall segment 64 is somewhat circumferentially wider than the arcuate edge 66.

Depending from the central portion 63 is a hollow cylindrical shaft 68, which includes an interiorly provided circular protrusion 70, whose purpose is hereinafter described. Between the shaft 68 and the skirt 71 are a plurality of radial ribs 78 depending from the spokelike portions 62 of the base portion 61. The side wall segments 64 also include ribs 69 projecting inwardly therefrom. The rib 69 provides additional strength to the side wall segments 64 and prevents same from warping or incurring other deformation. The ribs 69 furthermore secure pad 22 within the pad holder. The central portion 63 of the base portion 61 further includes an interior annular lip 73 that slopes downwardly towards the large aperture 80, said lip 73 including a plurality of slots 84, whose purpose is hereinafter described.

The emanator pad 22 is a coarse material, e.g., a die-cut felt material, provided preferably as two pads one above the other. The emanator pad may be inserted into the pad holder 20 by outwardly bending one of the side wall segments 64, which have sufficient flexibility and resiliency to allow such insertion. The pad holder may be made for example from polypropylene or high density polyethylene by conventional molding methods. The emanator pad may be made from woven or nonwoven materials capable of transporting liquids by capilary action, and preferably is a mixture of cotton, synthetic, and wood pulp fibers, plus a wet-strength binder.

Figure 2:
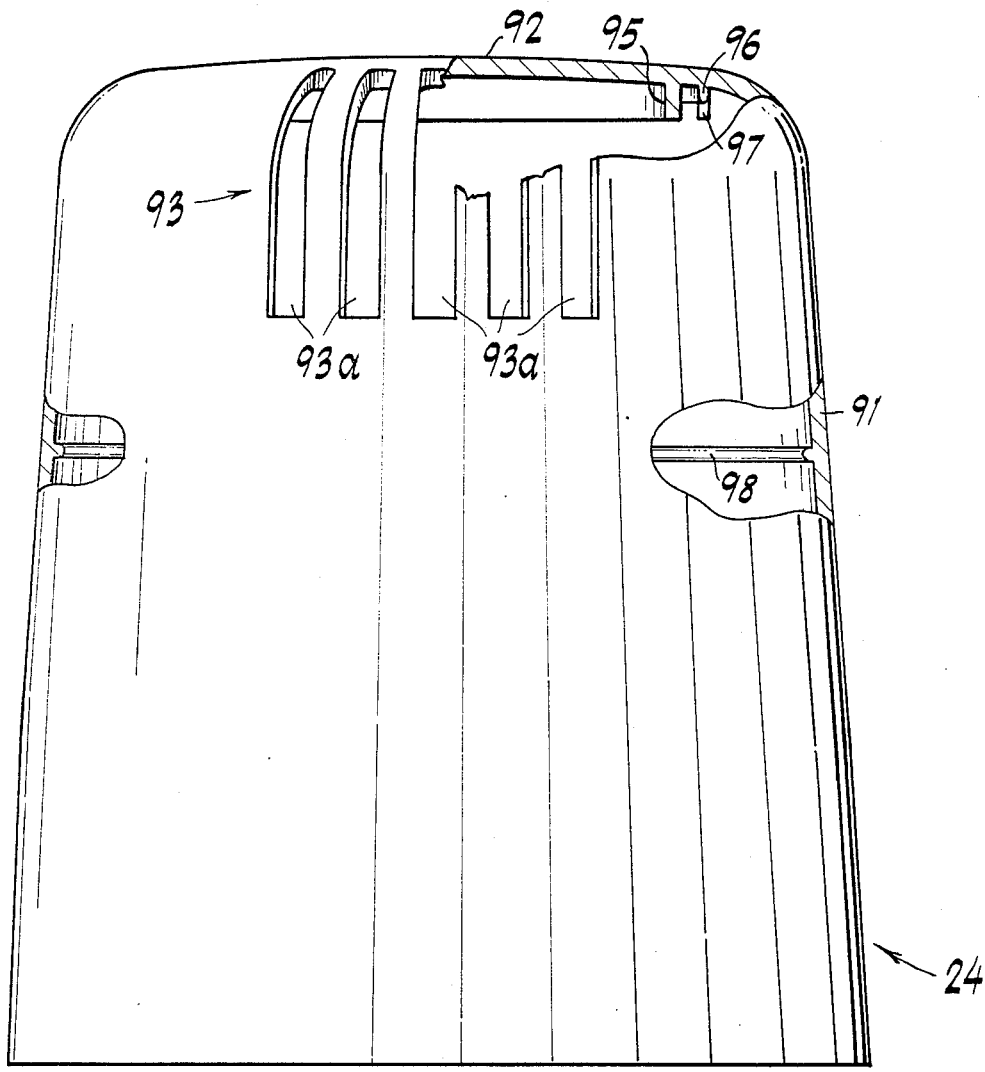
FIG. 2 is a partially broken away front view of the cover member of the air freshener dispenser shown in FIG. 1.
Figure 3:
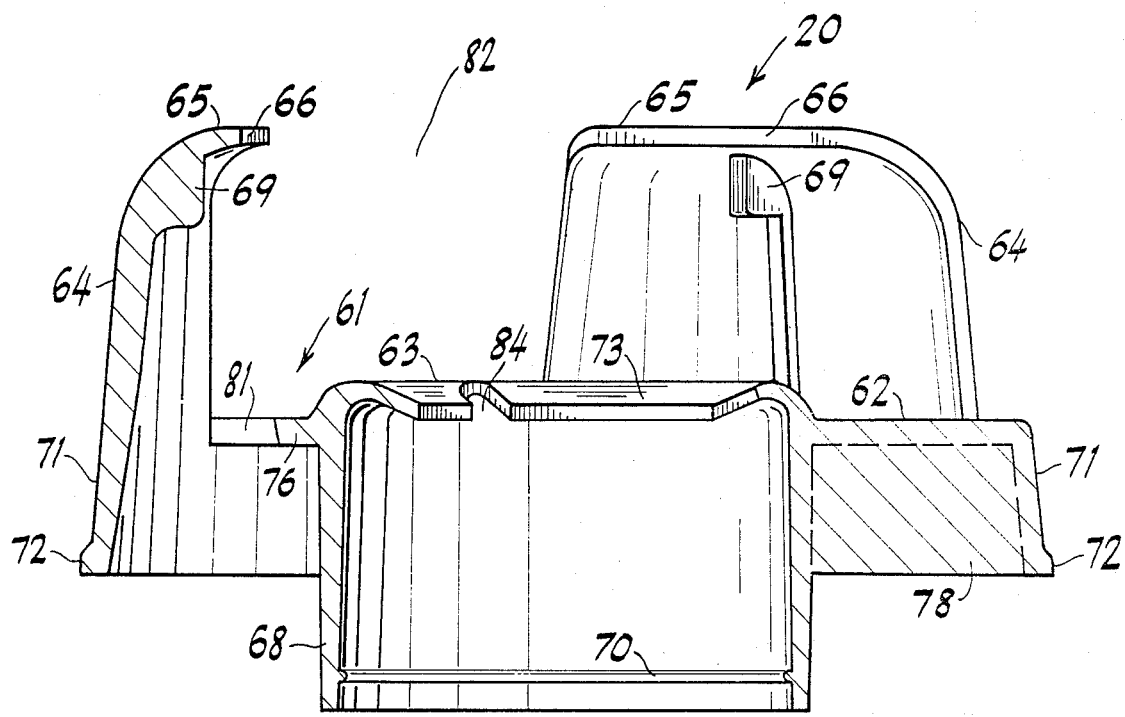
FIG. 3 is a cross-sectional view of the emanator pad holder across lines 3—3 of FIG. 4.
Figure 4:
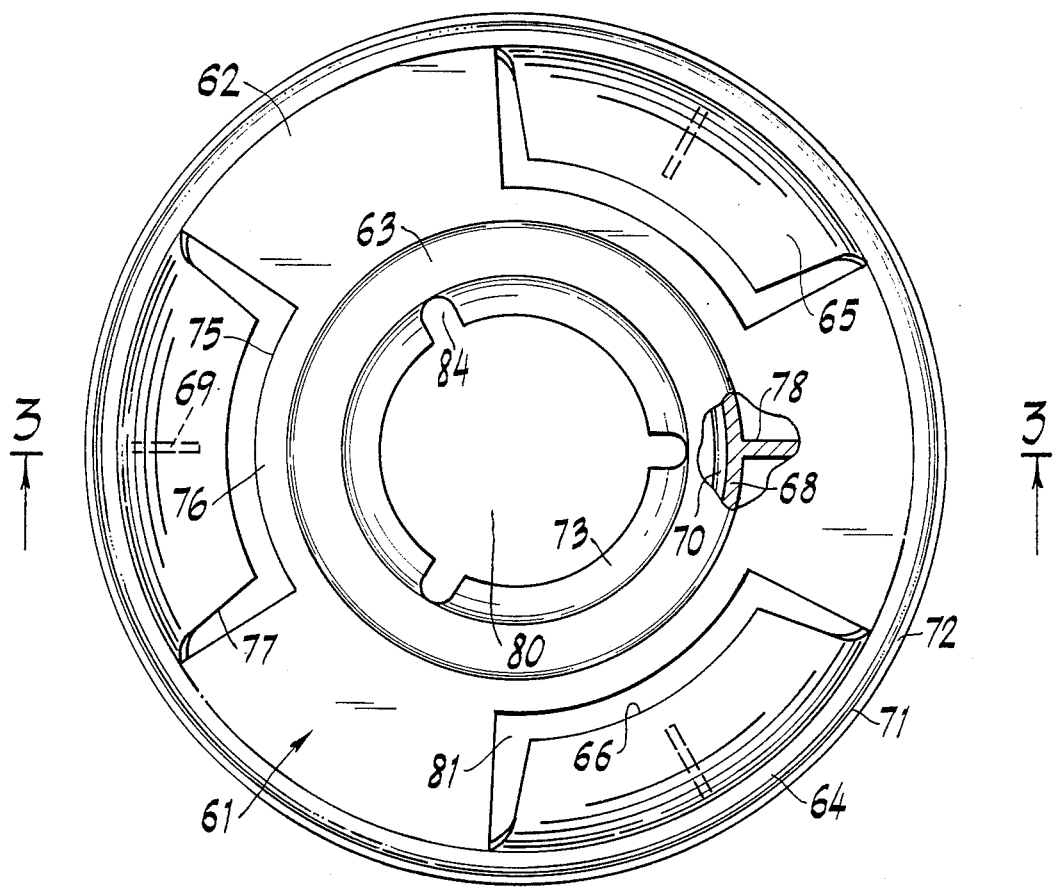
FIG. 4 is a top plan view of the emanator pad holder, a portion of which is broken away.

Referring to FIGS. 1 and 2, the cover member 24 comprises a slightly frustoconical body 91 including a top 92, there being a plurality of spaced apart air circulation apertures 93 through the body 91. Each of the apertures 93 may comprise a plurality of vertical slots 93a. Referring to FIG. 2, a partially broken-away front view of the cover member 24 an interior circular flange 95 depends from the top 92 of the cover member 24, and an exterior circular flange 96 also depends from the top 92 of the cover member 24, said exterior flange further including at least one stop member 97.

Referring to FIG. 5, the pad holder 20 (including the pads 22, not shown) is detachably retained within the cover member as follows: the emanator pad holder 20 is adapted for coincident placement proximate the top of the cover member 24. Thus, side wall segments 64 are essentially arcuately radially identical with the body 91 of the cover member. By urging the pad holder 20 towards the top 92, the arcuate edges 66 of the wall segments 64 engage the interior flange 95, as most easily understood by review of FIG. 5. The flexible and resilient side wall segments 64 flex outwardly slightly to achieve this mating. Similarly, peripheral boss 72 on the skirt 71 engages complementary boss 98 on the interior of the body 91 of the cover member 24. The emanator pad holder 20 is thereby rotatably engaged within the cover member 24. The circular flange 96 provides a rotation surface for the arcuate portion 65 of the side wall segment 64, with the stop member 97 being adapted to restrict rotation of the emanator pad holder 20 when the apertures 93 are in registry with the channels 82 or when the side wall segments 64 fully close the apertures 93. The emanator pad holder 20 (including the emanator pads 22) is secured within the cover member 24 during manufacture, and is intended to remain integrally assembled during shipment and use.

As indicated above, during shipment (or during nonuse) the closure cap 18 is connected to the neck 32 of the container 12. During this shipping or nonuse mode, the lower edge of the shaft 68 rests loosely on shoulder 54 of the closure cap in 18, the upstanding skirt 52 being received into the shaft 68, with the circular projection 70 providing additional frictional engagement.

To use the device, the consumer simply removes the cover member-emanator pad holder assembly, then removes the closure cap 18, and finally replaces said assembly. The shaft 68 receives the neck 32 of the container 12, and the complementary mating surfaces 34 and 70 are engaged. Furthermore, the circular lip 73 of the central base portion 63 flexes upwardly slightly, and compressively engages the top 42 of the insert member 14. The lip 73 is not especially resilient, but flexes in view of the flex slots 84 provided therein. The wick 16, in view of the connection between the container 12 and the pad holder 20, is in abutment with the emanator pad 22, and the fragrance composition may be wicked from the container 12 to the emanator pad 22.

The consumer may adjustably regulate the rate of diffusion of the fragrance material from the emanator pad to the atmosphere by rotationally opening or closing the cover member 12 to vary the size of the air circulation passages defined by the apertures 93 and the channels 82. Diffusion is enhanced by the provision of the updraft grooves 35 and the apertures 81, which provide a path for air flow to the vapor space above the emanator pad holder 20. Air contact with the bottom of the entire emanator pad is established by having the emanator pad rest on the raised central portion 63 of the base portion 61, thereby establishing an annular channel normal to the vertical axis of the device 10. The torquing force necessary to rotate the cover member 24 about the emanator pad 20-container 12 assembly is less than that required to rotate the emanator pad 20 about the emanator pad-container assembly. However, the emanator pad holder-cover assembly may rotate as one unit when the stop means 97 abut a side wall segment 64. This may be prevented by including a stop member on the interior surface of the shaft 68 that cooperates with flange 34, thereby limiting rotation.

It is to be understood that the air freshener device of the subject invention as well as its component parts may have or include parts or equivalents not specifically recited herein without departing from the spirit and scope of the claims appended below.

What is claimed is:

1. An air freshener dispenser comprising a container having an opening; a wick depending into the container; an emanator pad; emanator pad holding means detachably connected to the container and retaining the emanator pad in contact with the wick, said pad holding means including at least one fragrance diffusion channel and at least one upwardly extending side wall member; a cover member having a top and a substantially cylindrical side wall and including at least one fragrance diffusion aperture registrable with said fragrance diffusion channel, and retention means comprising a first mating surface associated with the pad holding means and a second mating surface associated with the cover member, said mating surface in operative position detachably retaining the cover member on the pad holding means, the first mating surface being inoperative in cooperation with said cover member substantially cylindrical side wall to detachably retain said cover member on the pad holding means, said cover member being rotatable in said detachably retained position with respect to said pad holding means, the pad holding means being nonrotatable with respect to the container by the torquing force for rotating the cover member on the pad holding means, whereby rotation of the cover member enables said at least one fragrance diffusion aperture and said at least one fragrance diffusion channel to be brought into registry.

2. The dispenser of claim 1, wherein the seocnd mating surface is a circular flange depending from the top of the cover member, and wherein the uppermost portion of the pad holding means side wall member curves inwardly towards the center of the pad holding means and terminates in an arcuate edge, said arcuate edge being said first mating surface, said uppermost portion of the side wall member being outwardly flexed when said arcuate edge is in mating relationship with said flange.

3. The dispenser of claim 1, wherein the pad holding means includes a planar base portion from which said side wall member upwardly extends and a peripheral skirt depending from said planar base portion, the skirt having a preipheral boss proximate its bottom edge, said boss being the first mating surface, and wherein the second mating surface is a peripheral boss on the interior surface of the substantially cylindrical side wall of the cover member, said first mating surface overlying said second mating surface in operative position.

4. The dispenser of claim 2, wherein the pad holding means includes a planar base portion from which said side wall member upwardly extends.

5. The dispenser of claim 3, wherein the uppermost portion of the pad holding means side wall member curves inwardly towards the center of the pad holding means.

6. The dispenser of claim 4 or 5, wherein the base portion of the pad holding means includes a central aperture through which the wick extends, the base portion further including a plurality of radial spokelike portions between the central aperture and the periphery of the base portion, thereby defining air circulation apertures in said base portion.

7. The dispenser of claim 6, wherein there is a plurality of pad holding means side wall members extending upwardly from the base portion, the number of fragrance diffusion apertures in the cover member being of the same number as said plural number of side wall members.

8. The dispenser of claim 7, wherein the pad holding means includes a hollow cylindrical shaft depending from proximate the periphery of the central aperture in the planar base portion, and wherein the container includes a neck, the shaft being detachably connected to the neck.

9. The dispenser of claim 7, wherein the base portion includes a raised area.

10. The dispenser of claim 7, further including emanator pad securing ribs radially extending from said side wall members towards said central aperture.

11. The air freshener dispenser of claim 1, further comprising closure means removably attachable to the container to seal the container opening during periods of nonuse.

12. The air freshener dispenser of claim 1, wherein the container has at least one updraft groove to establish a fluid pathway from between proximate the bottom of the container to proximate the top of the container.

13. An air freshener dispenser comprising a container having an opening; a wick depending into the container; an emanator pad; emanator pad holding means detachably connected to the container and retaining the emanator pad in contact with the wick, said pad holding means including a planar base portion having a central aperture through which said wick extends, at least one side wall member including a plurality of fragrance diffusion channels, said planar base portion having a plurality of radial spokelike portions between the central aperture and the periphery of the base portion and defining air circulation apertures therethrough; a cover member having a top and a substantially cylindrical side wall and including a plurality of fragrance diffusion apertures equal in number to the fragrance diffusion channels and registrable with said fragrance diffusion channels, and retention means operative to detachably retain the cover member on the pad holding means, said cover member being rotatable in said detachably retained position with respect to said pad holding means, the pad holding means being nonrotatable with respect to the container by the torquing force for rotating the cover member on the pad holding means, whereby rotation of the cover member enables said at least one frqgrance diffusion aperture an said at least one fragrance diffusion channel to be brought into registry.

14. The dispenser of claim 13, wherein said retention means comprise a first mating surface associated with the pad holding means and a second mating surface associated with the cover member, the first mating surface being inoperative in cooperation with said cover member substantially cylindrical side wall to detachably retain said cover member on the pad holding means.

15. The dispenser of claim 14, wherein the second mating surface is a circular flange depending from the top of the cover member, and wherein there is a plurality of pad holding means side wall members, the uppermost portions of the side wall members curving inwardly towards the center of the pad holding means and terminating in an arcuate edge, said arcuate edge being said first mating surface, said uppermost portion of the side wall members being outwardly flexed when in mating relationship with said flange.

16. The dispenser of claim 14, wherein the pad holding means further includes a peripheral skirt depending from said planar base portion, the skirt proximate its bottom edge having a peripheral boss which is the first mating surface, and wherein the second mating surface is a peripheral boss on the interior surface of the substantially cylindrical side wall of the cover member.

17. The dispenser of claim 16, wherein the uppermost portion of the pad holding means side wall member curves inwardly towards the center of the pad holding means.

18. The dispenser of claim 17, wherein there is a plurality of pad holding means side wall members extending upwardly from the base portion, the number of fragrance diffusion apertures in the cover member being of the same number as said plural number of side wall members.

19. The dispenser of claims 15 or 18, wherein the pad holding means includes a hollow cylindrical shaft depending from proximate the periphery of the central aperture in the planar base, and wherein the container includes a neck, the shaft being detachably connected to the neck.

20. The dispenser of claim 19, wherein the base portion includes a raised area.

21. The dispenser of claim 19, further including emanator pad securing ribs radially extending from said side wall members towards said central aperture.

* * * * *